United States Patent [19]

Freitag et al.

[11] Patent Number: 4,982,014

[45] Date of Patent: Jan. 1, 1991

[54] DIHYDROXYDIPHENYL CYCLOALKANES, THEIR PRODUCTION AND THEIR USE FOR THE PRODUCTION OF HIGH MOLECULAR WEIGHT POLYCARBONATES

[75] Inventors: Dieter Freitag, Krefeld; Uwe Westeppe, Mettmann; Claus H. Wulff, Krefeld; Karl-Herbert Fritsch, Bergisch-Gladbach; Carl Casser, Bonn; Günther Weymans, Leverkusen; Lutz Schrader, Krefeld; Werner Waldenrath, Cologne, all of Fed. Rep. of Germany

[73] Assignee: Bayer Aktiengesellschaft, Leverkusen, Fed. Rep. of Germany

[21] Appl. No.: 390,028

[22] Filed: Aug. 4, 1989

[30] Foreign Application Priority Data

Aug. 12, 1988 [DE] Fed. Rep. of Germany ....... 3827434
Aug. 12, 1988 [DE] Fed. Rep. of Germany ....... 3827435
Sep. 23, 1988 [DE] Fed. Rep. of Germany ....... 3832396
Nov. 1, 1988 [DE] Fed. Rep. of Germany ....... 3837090
Mar. 23, 1989 [DE] Fed. Rep. of Germany ....... 3909601

[51] Int. Cl.[5] ............................................. C07C 39/17
[52] U.S. Cl. .................................... 568/721; 568/718; 568/722; 568/727; 528/196
[58] Field of Search ............... 568/721, 727, 718, 722; 528/196

[56] References Cited

U.S. PATENT DOCUMENTS

| | | | |
|---|---|---|---|
| 2,069,560 | 2/1937 | Rothrock | 260/154 |
| 2,069,573 | 2/1937 | Bolton | 260/154 |
| 2,342,294 | 2/1944 | Niederl | 260/479 |
| 2,538,725 | 1/1951 | Johnson, Jr. et al. | 167/53.1 |
| 2,883,365 | 4/1959 | Mathes | 260/45.95 |
| 4,180,651 | 12/1979 | Mark | 528/202 |
| 4,371,691 | 2/1983 | Friedhofen et al. | 528/196 |
| 4,637,971 | 1/1987 | Takei et al. | 430/59 |

FOREIGN PATENT DOCUMENTS 0089801 9/1983 European Pat. Off.
0166834 1/1986 European Pat. Off.
0249963 12/1987 European Pat. Off.
0274092 7/1988 European Pat. Off.

*Primary Examiner*—Werren B. Lone
*Attorney, Agent, or Firm*—Joseph C. Gil; Aron Preis

[57] ABSTRACT

Dihydroxydiphenyl cycloalkanes corresponding to the formula

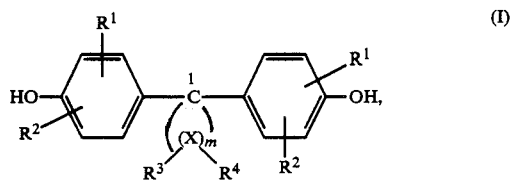

in which
$R^1$ and $R^2$ independently of one another represent hydrogen, halogen, $C_1$–$C_8$ alkyl, $C_5$–$C_6$ cycloalkyl, $C_6$–$C_{10}$ aryl and $C_7$–$C_{12}$ aralkyl,
m is an integer of from 4 to 7,
$R^3$ and $R^4$, individually selectable for each X, independently of one another represent hydrogen or $C_1$–$C_6$ alkyl
and
X represents carbon
with the proviso that, at at least one atom X, both $R^3$ and $R^4$ are alkyl, a process for their production, their use for the production of high molecular weight polycarbonates, the polycarbonates made from dihydroxydiphenyl cycloalkane of formula (I) and films made from these polycarbonates.

5 Claims, No Drawings

DIHYDROXYDIPHENYL CYCLOALKANES, THEIR PRODUCTION AND THEIR USE FOR THE PRODUCTION OF HIGH MOLECULAR WEIGHT POLYCARBONATES

This invention relates to dihydroxydiphenyl cycloalkanes corresponding to formula (I)

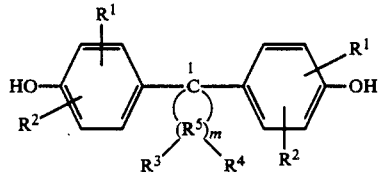
(I)

in which

R¹ and R² independently of one another represent hydrogen, halogen, preferably chlorine or bromine, $C_1$–$C_8$-alkyl, $C_5$–$C_6$-cycloalkyl, $C_6$–$C_{10}$-aryl, preferably phenyl, and $C_7$–$C_{12}$-aralkyl, preferably phenyl-$C_1$–$C_4$-alkyl, more particularly benzyl, m is an integer of from 4 to 7, preferably 4 or 5, R³ and R⁴, individually selectable for each R⁵, independently of one another represent hydrogen or $C_1$–$C_6$-alkyl and R⁵ represents carbon, with the proviso that, at at least one atom R⁵, both R³ and R⁴ are alkyl, Preferably at 1 or 2 atoms R⁵ and, more particularly, at only 1 atom R⁵, both R³ and R⁴ are alkyl. The preferred alkyl radical is methyl. The R⁵ atoms in the α-position to the diphenyl-substituted C atom (C-1) are preferably not dialkyl-substituted, whereas the R⁵, atoms in the β-position to C-1 are preferably dialkyl-substituted. More particularly, one R⁵-atom in the β-position to C-1 is dialkyl-substituted and one R⁵-atom in β′-position to C 1 is monoalkyl-substituted. More particularly the invention relates to dihydroxydiphenyl cyclohexanes containing 5 and 6 ring C atoms in the cycloaliphatic radical (m=4 or 5 in formula (I)), for example diphenols corresponding to the following formulae

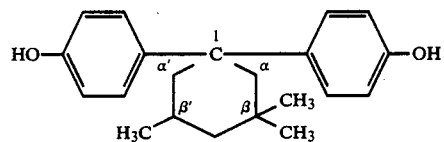
(II)

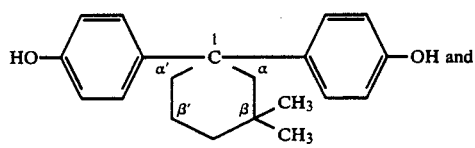
(III)

and

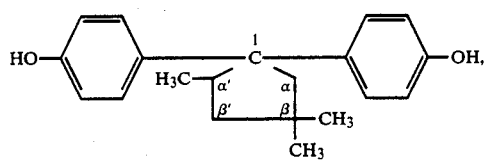
(IV)

the 1,1-bis-(4-hydroxyphenyl)-3,3,5-trimethyl cyclohexane (formula II) being particularly preferred.

The dihydroxydiphenyl cycloalkanes corresponding to formula (I) may be obtained in known manner by condensation of phenols corresponding to formula (V)

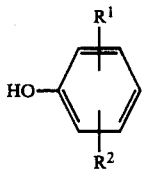
(V)

and ketones corresponding to formula (VI)

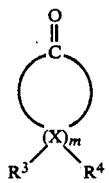
(VI)

where R⁵, R¹, R², R³, R⁴ and m are as defined for formula (I).

The phenols corresponding to formula (V) are either known or can be obtained by known methods (for cresols and xylenols, see for example Ullmanns Encyklopädie der technischen Chemie, 4th Revised and Extended edition, Vol. 15, pages 61–77, Verlag Chemie, Weinheim/New York, 1978; for chlorophenols, Ullmanns Encyklopädie der technischen Chemie, 4th Edition, Verlag Chemie, 1975, Vol. 9, pages 573–582; and for alkylphenols, Ullmanns Encyklopädie der technischen Chemie, 4th Edition, Verlag Chemie 1979, Vol. 18, pages 199–214).

Examples of suitable phenols corresponding to formula (V) are phenol, o-cresol, m-cresol, 2,6-dimethylphenol, 2-chlorophenol, 3-chlorophenol, 2,6-dichlorophenol, 2-cyclohexylphenol, 2,6-diphenylphenol and o-benzylphenol.

The ketones corresponding to formula (VI) are known (cf. for example Beilsteins Handbuch der Organischen Chemie, Vol. 7, 4th Edition, Springer-Verlag, Berlin, 1925 and the corresponding Supplementary Volumes 1 to 4 and J. Am. Soc. Vol. 79 (1975), pages 1488, 1492, US-PS 2,692,289; J. Chem. Soc., (1954), 2186–2192 and J. Org. Chem. Vol. 38, (1973), pages 4431–4435; J. Am. Chem. Soc. 87, (1965), pages 1353–1364. A general method for the production of ketones corresponding to formula (VI) is described, for example in "Organikum", 15th Edition, 1977, VEB-Deutscher Verlag der Wissenschaften, Berlin, for example on page 698.

The following are examples of known ketones corresponding to formula (VI): 3,3-dimethylcyclopentanone, 3,3-dimethylcyclohexanone, 4,4-dimethylcyclohexanone, 3-ethyl-3-methylcyclopentanone, 2,3,3-trimethylcyclopentanone, 3,3,4-trimethylcyclopentanone, 3,3-dimethylcycloheptanone, 4,4-dimethylcycloheptanone, 3-ethyl-3-methylcyclohexanone, 4-ethyl-4-methylcyclohexanone, 2,3,3-trimethylcyclohexanone, 2,4,4-trimethylcyclohexanone, 3,3,4-trimethylcyclohexanone, 3,3,5-trimethylcyclohexanone, 3,4,4-trimethylcyclohexanone, 2,3,3,4-tetramethylcyclopentanone, 3,3,5-trimethylcycloheptanone, 3,5,5-trimethylcycloheptanone, 5-ethyl-2,5-dimethylcycloheptanone, 2,3,3,5-tetramethylcycloheptanone, 2,3,5,5-tetramethylcycloheptanone, 3,3,5,5-tetramethylcycloheptanone, 4-ethyl-2,3,4-trimethylcyclopentanone, 3-ethyl-4-isopropyl-3-methylcyclopentanone, 4-sec.-butyl-3,3-dimethylcyclopentanone, 2-isopropyl-3,3,4-trimethylcyclopentanone, 3-ethyl-4-isopropyl-3-methyl-cyclohexanone, 4-ethyl-3-isopropyl-4-methylcyclohexanone, 3-sec.-butyl-4,4-dimethylcyclohexanone, 2-butyl-3,3,4-trimethylcyclopentanone, 2-butyl-3,3,4-trimethylcyclohexanone, 4-butyl-3,3,5-trimethylcyclohexanone, 3-isohexyl-3-methylcyclohexanone and 3,3,8-trimethylcyclooctanone.

The following are examples of preferred ketones:

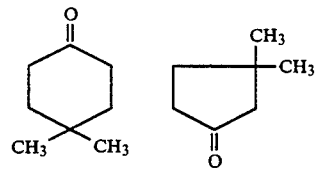

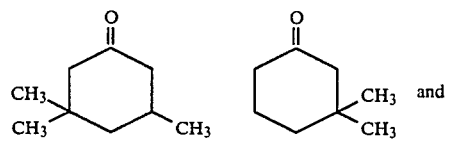

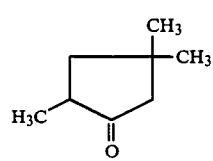

To prepare the bisphenols, the phenol (V) is generally used in a quantity of 2 to 10 mols and preferably in a quantity of 2.5 to 6 mols per mol ketone (VI). Preferred reaction times are from 1 to 100 hours. The reaction is generally carried out at a temperature in the range from −30° C. to 300° C. and preferably at a temperature in the range from −15° C. to 150° C. and under a pressure of from 1 to 20 bar and preferably under a pressure of from 1 to 10 bar.

The condensation is generally carried out in the presence of acidic catalysts such as, for example, hydrogen chloride, hydrogen bromide, hydrogen fluoride, boron trifluoride, aluminium trichloride, zinc dichloride, titanium tetrachloride, tin tetrachloride, phosphorus halides, phosphorus pentoxide, phosphoric acid, concentrated hydrochloric acid or sulfuric acid and also mixtures of acetic acid and acetanhydride. Acidic ion exchangers may also be used.

In addition, the reaction may be accelerated by addition of co-catalysts, such as $C_1$–$C_{18}$alkyl mercaptans, hydrogen sulfide, thiophenols, thio acids and dialkyl sulfides, f.e. in quantities of 0.01–0.4 mol/mol of ketone, particularly 0.05–0.02 mol/mol of ketone.

The condensation may be carried out in the absence of solvents or in the presence of an inert solvent (for example an aliphatic or aromatic hydrocarbon, chlorinated hydrocarbon).

In cases where the catalyst also acts as a dehydrating agent, there is no need to use separate dehydrating agents, although, to obtain good conversion, it is always of advantage to use dehydrating agents when the catalyst used does not bind the water of reaction.

Suitable dehydrating agents are, for example, acetanhydride, zeolites, polyphosphoric acid and phosphorus pentoxide.

Accordingly, the present invention also relates to a process for the production of the dihydroxydiphenyl cycloalkanes corresponding to formula (I)

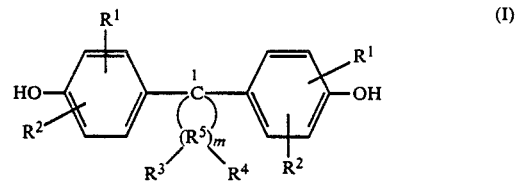

in which
R$^1$ and R$^2$ independently of one another represent hydrogen, halogen, preferably chlorine or bromine, $C_1$–$C_8$-alkyl, $C_5$–$C_6$ cycloalkyl, $C_5$–$C_{10}$-aryl, preferably phenyl, and $C_7$–$C_{12}$-aralkyl, preferably phenyl-$C_1$–$C_4$-alkyl, more particularly benzyl,
m is an integer of from 4 to 7, preferably 4 or 5,
R$^3$ and R$^4$, individually selectable for each R$^5$, independently of one another represent hydrogen or $C_1$–$C_6$-alkyl
and
R$^5$ represents carbon, with the proviso that, at least one atom R$^5$, both R$^3$ and R$^4$ are alkyl,
characterized in that phenols corresponding to formula (V)

in which
R$^1$ and R$^2$ are as defined for formula (I), are reacted with ketones corresponding to formula (VI)

in which
X, m, R$^3$ and R$^4$ are as defined for formula (I), in a molar ratio of (V):(VI) of from 2:1 to 10:1 and preferably in a molar ratio of from 2.5:1 to 6:1 at temperatures of −30° C. to 300° C., preferably −15° to 150° C. and under pressures of 1 to 10 bar in the presence of acidic catalysts and optionally in the presence of cocatalysts and/or solvents and/or dehydrating agents.

In formula (I), R$^3$ and R$^4$ are both alkyl at preferably 1 or 2 atoms X, but more especially at only 1 atom X. The preferred alkyl radical is methyl, although ethyl or linear or branched $C_3$–$C_6$-alkyl radicals may also be used. The X atoms in the α-position to the diphenyl-substituted C atom (C-1) are preferably not dialkyl-substituted, whereas the X atoms in the β-position to C-1 are preferably dialkyl-substituted. More particularly, one X atom in the $\beta$-position to C-1 is dialkyl-substituted and one X atom in the $\beta'$-position to C-1 is monoalkyl-substituted.

In some cases, the reaction is not entirely uniform, i.e. several different products can be formed, so that the desired compound first has to be isolated from a mixture. For particulars of the condensation, reference may be made to Schnell, Chemistry and Physics of Polycarbonates, Interscience Publishers, New York 1964. In some cases, it is possible to control the reaction through the choice of suitable catalysts and reaction conditions in such a way that the desired compound precipitates or crystallizes out, which makes it easier to isolate.

EXAMPLE A.1

Preparation of the diphenol of formula (II)

7.5 mol (705 g) phenol and 0.15 mol (30.3 g) dodecylthiol are introduced into a 1-liter round-bottomed flask equipped with a stirrer, dropping funnel, thermometer, reflux condenser and gas inlet pipe and saturated with dry HCl gas at 28° to 30° C. A solution of 1.5 mol (210 g) dihydroisophorone (3,3,5-trimethylcyclohexan-1-one) and 1.5 mol (151 g) phenol is added dropwise to the resulting solution over a period of 3 hours, HCl gas continuing to be passed through the reaction solution. After the addition, HCl gas is introduced for another 5 hours. The mixture is then left to react for 8 hours at room temperature. The excess phenol is then removed by steam distillation. The residue is hot-extracted twice with petroleum ether (60–90) and once with methylene chloride and filtered off. Yield: 370 g; Mp: 205°–207° C.

EXAMPLE A.2

Preparation of the diphenol of formula (II)

1692 g (18 mol) of phenol, 60.6 g (0.3 mol) of dodecylthiol and 420 g (3 mol) of dihydroisophorone (3,3,5-trimethylcyclohexan-1-one) are introduced into a stirring apparatus equipped with a stirrer, thermometer, reflux condenser and gas inlet pipe at 28°–30° C. Dry HCl gas is introduced into this solution over a period of 5 hours at 28°–30° C. The mixture is then left to react for about 10 h at 28°–30° C. When 95% of the ketone has been converted (examined by GC), 2.5 l of water are added to the reaction mixture and a pH value of 6 is adjusted by adding a 45% NaOH solution. The reaction mixture is stirred for one hour at 80° C. and then cooled to 25° C. The aqueous phase is decanted off and the remaining residue is washed with water at 80° C. The resulting crude product is filtered off and hot-extracted twice with n-hexane and twice with methylene chloride and then filtered. The residue is recrystallised twice from xylene.

Yield: 753 g
Melting point: 209°–211° C.

EXAMPLE A.3

Preparation of the diphenol of formula (II)

564 (6 mol) of phenol, 10.8 g (0.12 mol) of butanethiol and 140 g (1 mol) of dihydroisophorone (3,3,5-trimethylcyclohexan-1-one) are introduced into a stirring apparatus equipped with a stirrer, thermometer, reflux condenser and gas inlet pipe at 30° C. At this temperature 44 g of 37% HCl are added. The reaction mixture is stirred for about 70 h at 28°–30° C. When 95% of the ketone has been converted (examined by GC) 2 l of water are added to the reaction mixture and a pH value of 6 is adjusted by adding a 45% NaOH solution. The reaction mixture is stirred for one hour at 80° C. and then cooled to 25° C. The aqueous phase is decanted off and the remaining residue is washed with water at 80° C. The resulting crude product is filtered off and hot-extracted twice with n-hexane and twice with toluene and then filtered at 30° C.

Yield: 253 g
Melding point: 205°–208° C.

EXAMPLE A.4

Preparation of the diphenol of the formula (Ib)($R^1$ and $R^2=CH_3$)

2196 g (18 mol) of 2,6-dimethylphenol, 38.2 g (0.36 mol) of $\beta$-mercaptopropionic acid and 420 g (3 mol) of dihydroisophorone (3,3,5-trimethylcyclohexan-1-one) are introduced into a stirring apparatus equipped with a stirrer, thermometer, reflux condenser and gas inlet pipe at 35° C. Dry HCl gas is introduced into this solution at 35° C. over a period of 5 h. The mixture is then left to react at 28°–30° C. for a period of about 10 hours. When 95% of the ketone has been converted (examined by GC) 2.5 l of water are added to the reaction mixture and a pH value of 6 is adjusted by the addition of a 45% NaOH solution. The reaction mixture is stirred for one hour at 80° C. and then cooled to room temperature. The aqueous phase is decanted off and the remaining residue is washed with water at 60° C. The resulting crude product is filtered off and hot-extracted three times with n-hexane and is then filtered.

Yield: 856 g
Melting point: 236°–238° C.

EXAMPLE A.5

Preparation of the diphenol of formula (III)

Following the same procedure as in Example A.2 3 mol of 3,3-dimethylcyclohexanone are used instead of 3 mol of dihydroisophorone. The product had a melting point of 190°–201° C.

The diphenols of formula (I) according to the invention are particularly suitable for the production of high molecular weight, thermoplastic polycarbonates which are distinguished by high heat resistance in combination with other favorable properties.

Accordingly, the present invention also relates to the use of the diphenols of formula (I) for the production of high molecular weight thermoplastic, aromatic polycarbonates.

It is possible to use both a single diphenol corresponding to formula (I), in which case homopolycarbonates are formed, and also several diphenols corresponding to formula (I), in which case copolycarbonates are formed.

In addition, the diphenols corresponding to formula (I) may also be used in admixture with other diphenols, for example with those corresponding to the formula HO—Z—OH (VII), for the production of high molecular weight, thermoplastic aromatic polycarbonates.

Suitable other diphenols corresponding to the formula H—Z—OH (VII) are those in which Z is an aromatic radical containing 6 to 30 C atoms which may contain one or more aromatic nuclei, may be substituted and may contain aliphatic radicals or other cycloaliphatic radicals than those corresponding to formula (I) or heteroatoms as bridge members.

Examples of diphenols corresponding to formula (VII) are hydroquinones, resorcinol, dihydroxydiphenyls, bis-(hydroxyphenyl)-alkanes, bis-(hydroxyphenyl)-cycloalkanes, bis-(hydroxyphenyl)-sulfides, bis-(hydroxyphenyl)-ethers, bis-(hydroxyphenyl)-ketones, bis-(hydroxyphenyl)-sulfones, bis-(hydroxyphenyl)-sulfoxides, α,α'-bis-(hydroxyphenyl)-diisopropylbenzenes and nucleus-halogenated compounds thereof.

These and other suitable other diphenols are described, for example, in US-PS 3,028,365, 2,999,835, 3,148,172, 3,275,601, 2,991,273, 3,271,367, 3,062,781, 2,970,131 and 2,999,846; in DE-OS 1 570 703, 2 063 050, 2 063 052, 2 211 0956, in FR-PS 1 561 518 and in the book by H. Schnell entitled "Chemistry and Physics of Polycarbonates", Interscience Publishers, New York, 1964.

Preferred other diphenols are, for example 4,4'-dihydroxydiphenyl, 2,2-bis-(4-hydroxyphenyl)-propane, 2,4-bis-(4-hydroxyphenyl)-2-methylbutane, 1,1-bis-(4-hydroxyphenyl)-cyclohexane, α,α'-bis-(4-hydroxyphenyl)-p-diisopropylbenzene, 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-cyclohexane, α,α'-bis-(3,5-dimethyl-4-hydroxyphenyl)-p-diisopropylbenzene, 2,2-bis-(3,5-dichloro-4-hydroxyphenyl)-propane and 2,2-bis-(3,5-dibromo-4-hydroxyphenyl)-propane.

Particularly preferred diphenols corresponding to formula (VII) are, for example, 2,2-bis-(4-hydroxyphenyl)-propane, 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane and 1,1-bis-(4-hydroxyphenyl)-cyclohexane.

2,2-Bis-(4-hydroxyphenyl)-propane is particularly preferred.

The other diphenols may be used both individually and in admixture with one another.

The molar ratio of diphenols corresponding to formula (I) to the other diphenols optionally used, for example those corresponding to formula (VII), is from 100 mol-% (I) and 0 mol-% other diphenol to 2 mol-% (I) and 98 mol-% other diphenol, preferably from 100 mol-% (I) and 0 mol-% other diphenol to 5 mol-% (I) and 95 mol-% other diphenol and, more preferably, from 100 mol-% (I) and 0 mol-% other diphenol to 10 mol-% (I) and 90 mol-% other diphenol and, most preferably, from 100 mol-% (I) and 0 mol-% other diphenol to 20 mol-% (I) and 80 mol-% other diphenol.

The high molecular weight polycarbonates of the diphenols corresponding to formula (I), optionally in combination with other diphenols, may be prepared by any of the known methods used to produce polycarbonates. The various diphenols may be attached to one another both statistically and also in blocks.

Accordingly, the present invention also relates to a process for the production of high molecular weight, thermoplastic aromatic polycarbonates from diphenols, optionally chain terminators and optionally branching agents by the known methods for the production of polycarbonates, preferably by phase interface polycondensation, wherein diphenols of formula (I) are used as the diphenols in quantities of from 100 mol-% to 2 mol-%. preferably in quantities of from 100 mol-% to 5 mol-%, more preferably in quantities of from 100 mol-% to 10 mol-% and most preferably in quantities of from 100 mol-% to 20 mol-%, based on the total mols diphenols used.

The branching agents used, if any, are known and constitute small quantities, preferably of from 0.05 to 2.0 mol-% (based on diphenols used), of trifunctional or more than trifunctional compounds, particularly those containing three or more than three phenolic hydroxyl groups. Branching agents containing three or more than three phenolic hydroxyl groups include phoroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis-(4,4-bis-(4-hydroxyphenyl)-cyclohexyl)-propane, 2,4-bis-(4-hydroxyphenylisopropyl)-phenol, 2,6-bis-(2-hydroxy-5'-methylbenzyl)-4-methylphenol, 2-(4-hydroxyphenyl)-2-(2,4-dihydroxyphenyl-propane, hexa-(4-(4-hydroxyphenylisopropyl)-phenyl)-orthoterephthalic acid ester, tetra-(4-hydroxyphenyl)-methane, tetra-(4-(4-hydroxyphenylisopropyl)-phenoxy)-methane and 1,4-bis-(4',4''-dihydroxytriphenyl)-methyl-benzene.

Some of the other trifunctional compounds are 2,4-dihydroxybenzoic acid, trimesic acid, cyanuric chloride and 3,3-bis-(3-methyl-4-hydroxyphenyl)-2-oxo-2,3-dihydroindole.

Monofunctional compounds may be used in the usual concentrations as chain terminators for regulating the molecular weight of the polycarbonates (a) in known manner. Suitable compounds are, for example, phenol, tert.-butylphenols or other alkyl-$C_1$-$C_7$-substituted phenols. Small quantities of phenols corresponding to formula (VIII)

(VIII)

in which R is a branched $C_8$ and/or $C_9$ alkyl radical, are particularly suitable for regulating molecular weight. In the alkyl radical R, the percentage of protons in $CH_3$-groups is 47 to 89% and the percentage of protons in CH- and $CH_3$-groups is 53 to 11%. R is preferably in the o- and/or p-position to the OH group, 20% being the particularly preferred upper limit to the ortho component. The chain terminators are generally used in quantities of 0.5 to 10 mol-% and preferably in quantities of 1.5 to 8 mol-%, based on the diphenols used.

The polycarbonates according to the invention can be produced in known manner, preferably by the phase interface polycondensation process (cf. H. Schnell "Chemistry and Physics of Polycarbonates", Polymer Reviews, Vol, IX, pages 33 et seq, Interscience Publ., 1964). In this process, the diphenols corresponding to formula (I) are dissolved in an aqueous alkaline phase. To prepare copolycarbonates with other diphenols, mixtures of diphenols corresponding to formula (I) and the other diphenols, for example those corresponding to formula (VII), are used. Chain terminators, for example corresponding to formula (VIII), may be added to regulate molecular weight. The reaction is then carried out with phosgene by the phase interface polycondensation method in the presence of an inert, preferably polycarbonate-dissolving, organic phase. The reaction temperature is in the range from 0° to 40° C.

The branching agents optionally used (preferably 0.05 to 2 mol-%) may be initially introduced either with the diphenols in the aqueous alkaline phase or may be added in solution in the organic solvent before the phosgenation.

In addition tot he diphenols of formula (I) and, optionally, other diphenols (VII), mono- and/or bis-chlorocarbonic acid esters thereof may also be used, being added in solution in organic solvents. The quantity of chain terminators and branching agents used is then determined by the molar quantity of diphenolate residues corresponding to formula (I) and, optionally, formula (VII). Where chlorocarbonic acid esters are used, the quantity of phosgene may be reduced accordingly in known manner.

Suitable organic solvents for the chain terminators and, optionally, for branching agents and the chlorocarbonic acid esters are, for example, methylene chloride, chlorobenzene, acetone, acetonitrile and mixtures of these solvents, particularly mixtures of methylene chloride and chlorobenzene. The chain terminators and branching agents used may optionally be dissolved in the same solvent.

The organic phase for the phase interface polycondensation may be formed, for example, by methylene chloride, chlorobenzene and by mixtures of methylene chloride and chlorobenzene.

Aqueous NaOH solution for example is used as the aqueous alkaline phase.

The production of the polycarbonates according to the invention by the phase interface polycondensation process can be catalyzed in the usual way by such catalysts as tertiary amines, particularly tertiary aliphatic amines, such as tributylamine or triethylamine. The catalysts may be used in quantities of 0.05 to 10 mol-%, based on mols diphenols used. The catalysts may be added before the beginning of phosgenation or during or even after phosgenation.

The polycarbonates according to the invention are recovered in known manner.

The high molecular weight, thermoplastic aromatic polycarbonates according to the invention may also be produced by the known homogeneous-phase process, the so-called "pyridine process" and also by the known melt transesterification process using diphenyl carbonate for example instead of phosgene. In this case, too, the polycarbonates according to the invention are isolated in known manner.

The polycarbonate obtainable by the process according to the invention preferably have molecular weights Mw (weight average, as determined by gel chromatography after preliminary calibration) of at least 10,000 g/mol, and particularly preferably of 10,000 to 300,000 g/mol. Where the polycarbonates according to the invention are used as injection-moulding materials, molecular weights of from 20,000 to 80,000 g/mol are particularly preferred. Where the polycarbonates according to the invention are used as cast films molecular weights Mw of from 100,000 to 250,000 g/mol are particularly preferred. For the production of extrusion films polycarbonates according to the invention with Mw of from 25,000 to 150,000 g/mol are preferred. The polycarbonates according to the invention can be linear or branched; they are homo-polycarbonates or co-polycarbonates based on the diphenols of formula (I).

Accordingly, the present invention also relates to high molecular weight, thermoplastic, aromatic polycarbonates having $\overline{M}w$ values (weight average molecular weights) of at least 10,000, preferably in the range from 10,000 to 300,000 g/mol and more preferably, in the case of injection moulding applications, in the range from 20,000 to 80,000 which contain bifunctional carbonate structural units corresponding to formula (Ia)

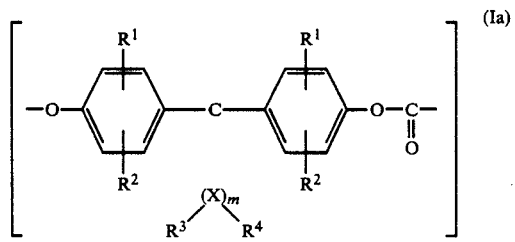

in which
X, $R^1$, $R^2$, $R^3$, $R^4$ and m are as defined for formula (I), in quantities of from 100 mol-% to 2 mol-%, preferably in quantities of from 100 mol-% to 5 mol-%, more preferably in quantities of from 100 mol-% to 10 mol-% and, most preferably, in quantities of from 100 mol-% to 20 mol-%, based in each case on the total quantity of 100 mol-% of difunctional carbonate structural units in the polycarbonate.

The polycarbonates according to the invention contain quantities - complementary in each case to 100 mol-% - of other difunctional carbonate structural units, for example those corresponding to formula (VIIa)

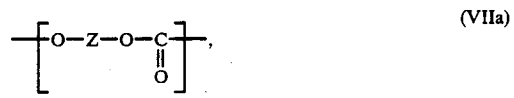

i.e. in quantities of from 0 mol-% (inclusive) to 98 mol-% inclusive, preferably from 0 mol-% to 95 mol-%, more preferably from 0 mol-% to 90 mol-% and most preferably from 0 mol-% to 80 mol-%, based in each case on the total quantity of 100 mol-% of difunctional carbonate structural units in the polycarbonate.

Polycarbonates based on cycloaliphatic bisphenols are basically known and are described, for example, in EP-A 164 476, DE-OS 3 345 945, DE-OS 2 063 052, FR 1 427 998, WO 8 000 348, BE-PS 785 189. They frequently have relatively high glass transition temperatures, but other important physical properties, such as UV stability and heat ageing resistance are not sufficient.

It has been surprisingly found that, as already mentioned, it is possible by incorporation of the diphenols of formula (I) according to the invention to obtain new polycarbonates combining high heat resistance with other favorable properties. This applies in particular to the polycarbonates based on the diphenols (I), in which m is 4 or 5, and more particularly to the polycarbonates based on diphenols corresponding to formula (Ib)

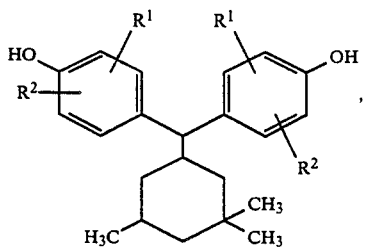

in which
R[1] and R[2] independently of one another have the meaning defined for formula (I) and, more preferably, represent hydrogen.

Accordingly, the present invention preferably relates to polycarbonates, wherein m=4 or 5 in the structural units corresponding to formula (Ia) and, more especially, to those containing units corresponding to formula (Ic)

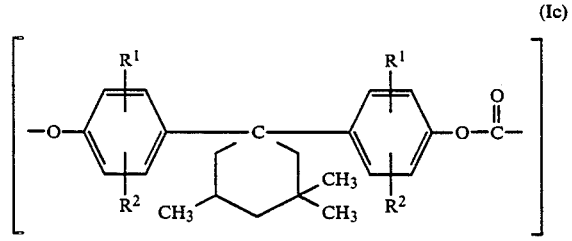

in which
R[1] and R[2] are as defined for formula (Ia), but are preferably hydrogen.

These polycarbonates based on the diphenols corresponding to formula (Ib), in which R[1] and R[2] are preferably hydrogen, also show high UV stability and good flow behavior in the melt in addition to their high heat resistance.

In addition, the properties of the polycarbonates may be varied with advantage through combination with other diphenols, particularly with the diphenols corresponding to formula (VII).

The polycarbonates obtainable by the process according to the invention are recovered in known manner by separating off the organic phase generated in the phase interface polycondensation process, washing it until it is neutral and electrolyte-free and then isolating it as granulate, for example in an evaporation extruder.

The additives normally used for thermoplastic polycarbonates, such as stabilizers, mold release agents, pigments, flameproofing agents, antistatic agents, fillers and reinforcing materials may be added in the usual quantities to the polycarbonates according to the invention before or after their processing.

More particularly, it is possible to add, for example, carbon black, graphite, kieselgur, kaolin, clays, $CaF_2$, $CaCO_3$, aluminium oxides, glass fibers, $BaSO_4$ and inorganic pigments both as fillers and as nucleating agents and, for example, glycerol stearates, pentaerythritol tetrastearate and trimethylol propane tristearate as mold release agents.

The polycarbonates according to the invention may be processed to moldings, for example by extruding the polycarbonates isolated in known manner to granulate and processing the resulting granulate in known manner by injection molding to form various articles, optionally after incorporation of the additives mentioned above.

The polycarbonates according to the invention may be used as moldings for any applications where hitherto known polycarbonates are used, i.e. both in the electrical field and in the building field for covering and glazing purposes, particularly when high heat resistance coupled with good processibility are required, i.e. when complicated components of high heat resistance are required.

Additional uses of the polycarbonates of the invention are as follows:

A. as optical data recording members, such as compact discs:

The manufacture of such recording members is known (see for example: J. Hennig, Lecture at the symposium on "New Polymers" in Bad Nauheim on 14/15.4.1980 "Polymers as substrates for optical disc memories" or Philips techn. Rev. 33, 178–180, 1973, No. 7 and 33, 186–189, 1973 No. 7).

B. for the manufacture of safety panes.

Safety panes usually have a thickness of 2 mm to 10 mm and can be vapour-coated with $SiO_x$, wherein x has a value of 1 or 2, or can be used in conjunction with glass panes. As is known, safety panes are necessary in many sections of buildings, vehicles and aeroplanes and are useful as shields and helmets.

C. as raw materials for lacquers.

D. for the production of blown articles (see for example U.S. Pat. No. 2,964,794).

E. for the production of transparent panels, in particular hollow space panels for example for covering buildings such as railway stations, greenhouse and lighting installations.

F. for the production of foams (see for example DE-AS 1,031,507).

G. for the production of filaments and wires (see for example DE-AS 1,137,167 and DE-OS 1,785,137).

H. as translucent plastics containing glass fibres, for lighting purposes, (see for example DE-OS 1,544,920).

I. for the production of small injection-moulded precision parts, such as for example lense holders. For this purpose polycarbonates are used which have a content of glass fibres and optionally additionally contain about 1% by weight of $MoS_2$, based on the total weight (see for example DE-OS 2,344,737).

K. for the production of parts for optical instruments, in particular lenses for photographic and cine cameras, (see for example DE-OS 2,701,173).

L. as light transmission carriers in particular as light guides (see for example EP-OS 0 089 801).

M. as electrical insulating materials for electrical conductors.

O. as a carrier material for organic photoconductors.

P. for the production of lamps, such as for example head lamps or light scattering discs.

The high molecular weight aromatic polycarbonates of the invention can be used particularly for the production of films. The films have preferred thicknesses of from 1 to 1500 μm and particularly preferred thicknesses of from 10 to 900 μm.

The films obtained can be monoaxially or biaxially stretched in known manner, preferably in a ratio of from 1:1.5 to 1:3.

The films may be produced by known methods for the production of films, for example by extrusion of a polymer melt through a flat film die, by blowing in a film blowing machine, deep drawing or casting. For casting, a concentrated solution of the polymer in a suitable solvent is cast onto a flat substrate, the solvent is evaporated and the film formed is lifted off the substrate.

The films can be stretched in known manner on known machines at temperatures from room temperature to a temperature at which the viscosity of the polymer melt is still not too greatly reduced and in general at temperatures up to about 370° C.

In order to produce the films by casting concentrated solutions of the polycarbonate in a suitable solvent can be poured onto level surfaces and, while maintaining the level surfaces at a temperature of from room temperature to 150° C., the solvent is evaporated. The concentrated solutions of the polycarbonates can also be poured onto liquids which have a higher density than that of the polycarbonate solutions, are not compatible with the solvent employed and do not dissolve the polycarbonate, and, after spreading out the solutions, the films are obtained by evaporating the solvent used for the polycarbonate and optionally also the liquid having a higher density.

The films according to the invention have a particularly high dimensional stability at elevated temperature and exhibit selective permeability to many gases. They can therefore be advantageously used as membranes for gas permeation.

It is of course also possible to use them for producing composite films with other plastic films; basically all known films are suitable as the second films, depending on the desired application and final properties of the composite film. A composite of two or more films can be made e.g. by placing the individual films, including the polycarbonate film according to the invention, on top of each other and pressing them together at an elevated temperature governed by the softening points of the individual films. It is also possible to use the known film co-extrusion process.

The composite films can be produced in practice by first making films of the components in a known manner or in the abovedescribed manner with optimum temperature control. Then the still hot films are brought to a common temperature without being stretched to any great degree, this temperature preferably being between room temperature and 370° C. The films are then brought together via rollers and pressed together for a short time. A pressure of between 2 and 500 bar can be applied for this purpose. The process can also be carried out with more than one other film than that composed of the polycarbonates; in this case the other films are for example first brought together in a manner hitherto known and are then pressed together with the polycarbonate film under the pressure described above.

The film or composite films can also be produced and used in known manner in the form of homogeneous membranes, composition membranes or asymmetric membranes. The membranes, films or composite films can be flat, can form hollow articles of various geometrical shapes - cylindrical, spherical or tubular - or can also be in the form of hollow fibres. Such moulded articles can be produced by known methods.

Depending on the application envisaged various polymers as exemplified below can be used for making films for the production of composites containing the polycarbonate films according to the invention. Again depending on the application composite films can be obtained which are impermeable to gas and have improved dimensional stability under heat compared with the prior art, or those which are dimensionally stable under heat and are permeable to gas -by suitable selecting the other films in the composite.

Polymers yielding films to be combined with the films according to the invention are described in the following. These poylmers are referred to as component (b).

Thermoplastics suitable as component (b) are both (b1) amorphous thermoplastics, preferably those having a glass temperature of more than 40° C. and more especially in the range from 60° C. to 220° C., and also (b2) partially crystalline thermoplastics, preferably those having a melting temperature of more than 60° C. and more especially in the range from 80° C. to 400° C. Elastomers for components (b) are (b3) polymers which have a glass temperature below 0° C., preferably below −10° C. and more especially in the range from −15° C. to −140° C.

Examples of amorphous thermoplastics (b1) are amorphous polymers from the class of polycarbonates, polyamides, polyolefins, polysulfones, polyketones, thermoplastic vinyl polymers, such as polymethyl acrylates, or homopolymers of aromatic vinyl compounds, copolymers of aromatic vinyl compounds or graft polymers of vinyl monomers of rubbers, polyethers, polyimides, thermoplastic polyurethanes, aromatic polyester (carbonates) and liquid crystalline polymers.

Examples of crystalline thermoplastics (b2) are aliphatic polyesters, polyarylene sulfides and the partially crystalline representatives of the thermoplastics listed above under (b1).

Examples of elastomers (b3) are the various rubbers, such as ethylene-propylene rubber, polyisoprene, polychloroprene, polysiloxanes, atactic polypropylene, diene, olefin and acrylate rubbers and natural rubbers, styrene-butadiene block copolymers, copolymers of ethylene with vinyl acetate or with (meth)acrylates, elastic polyurethanes, unless listed as thermoplastics under (b1) or (b2), and elastic polycarbonate-polyether block copolymers.

Amorphous thermoplastics (b1) are, in particular polycarbonates other than those according to the invention. These other polycarbonates may be both homopolycarbonates and also copolycarbonates and may be both linear and branched. The particularly preferred bisphenol for the polycarbonates is bisphenol A [=2,2-bis-(4-hydroxyphenyl)-propane].

These other thermoplastic polycarbonates are known.

The molecular weights $\overline{M}w$ (weight average molecular weight, as determined by gel permeation chromatography in tetrahydrofuran) of the other thermoplastic polycarbonates are in the range from 10,000 to 300,000 and preferably in the range from 12,000 to 150,000.

The thermoplastic polycarbonates can be used both individually and in admixture as component (b).

Preferred other thermoplastics for component (b) for the production of the mixtures according to the invention are also aliphatic, thermoplastic polyesters, more preferably polyalkylene terephthalates, i.e. for example those based on ethylene glycol, propane-1,3-diol, butane-1,4-diol, hexane-1,6-diol and 1,4-bis-hydroxymethylcyclohexane.

The molecular weights ($\overline{M}w$) of these polyalkylene terephthalates are in the range from 10,000 to 80,000.

The polyalkylene terephthalates may be obtained by known methods, for example from terephthalic acid dialkyl ester and the corresponding diol by transesterification (cf. for example US-PSS 2,647,855, 2,643,989, 2,534,028, 2,578,660, 2,742,494, 2,901,466).

Preferred other thermoplastics also include thermoplastic polyamides.

Suitable thermoplastic polyamides are any partially crystalline polyamides, particularly polyamide-6, polyamide-6,6, and partially crystalline copolyamides based on these two components. Other suitable thermoplastic polyamides are partially crystalline polyamides of which the acid component consists completely or in part of, in particular, adipic acid or caprolactam of terephthalic acid and/or isophthalic acid and/or suberic acid and/or sebacic acid and/or azelaic acid and/or dodecane dicarboxylic acid and/or adipic acid and/or cyclohexane dicarboxylic acid, and of which the diamine component consists completely or in part of, in particular, m- and/or p-xylylenediamine and/or hexamethylenediamine and/or 2,2,4- and/or 2,4,4-trimethyl hexamethylenediamine and/or isophoronediamine and/or 1,4-diaminobutane and of which the compositions are known in principle from the prior art (cf. for example Encyclopedia of Polymers, Vol. 11, pages 315 et seq.).

Other suitable thermoplastic polyamides are partially crystalline polyamides produced completely or in part from lactams containing 6 to 12 carbon atoms, optionally using one or more of the starting components mentioned above.

Particularly preferred partially crystalline polyamides are polyamide-6 and polyamide-6,6 or copolyamides containing a small amount (up to about 10% by weight) of other co-components.

Suitable polyamides are also amorphous polyamides obtained, for example, by polycondensation of diamines such as for example hexamethylenediamines, decamethylenediamine, 2,2,4- and 2,4,4-trimethyl hexamethylenediamine, m- or p-xylylenediamine, bis-(4-aminocyclohexyl)-methane, mixtures of 4,4'- and 2,2'-diaminodicyclohexyl methanes, 2,2-bis-(4-aminocyclohexyl)-propane, 3,3'-dimethyl-4,4'-diaminodicyclohexyl methane, 3-aminoethyl-3,5,5-trimethyl cyclohexyl amine, 2,5-bis-(aminomethyl)-norbornane, 2,6-bis-(aminomethyl)-norbornane, 1,4-diaminomethyl cyclohexane, and of mixtures of these diamines, with dicarboxylic acids, such as for example oxalic acid, adipic acid, azelaic acid, decane dicarboxylic acid, heptadecane dicarboxylic acid, 2,2,4-trimethyl adipic acid, 2,4,4-trimethyl adipic acid, isophthalic acid and terephthalic acid, and with mixtures of these dicarboxylic acids. Accordingly, amorphous copolyamides obtained by polycondensation of several of the diamines and/or dicarboxylic acids mentioned above are also included. Amorphous copolyamides prepared using ω-aminocarboxylic acids, such as ω-aminocaproic acid, ω-aminoundecanoic acid or ω-aminolauric acid, or lactams thereof, are also included.

Particularly suitable amorphous, thermoplastic polyamides are those obtainable from isophthalic acid, hexamethylenediamine and other diamines, such as 4,4'-diaminodicyclohexyl methane, isophorondiamine, 2,2,4- and 2,4,4-trimethyl hexamethylenediamine, 2,5- and/or 2,6-bis-(aminomethyl)-norbornane; those obtainable from isophthalic acid, 4,4'-diaminodicyclohexyl methane and ω-caprolactam; those obtainable from isophthalic acid, 3,3-dimethyl-4,4'-diaminodicyclohexyl methane and ω-lauric lactam; and those obtainable from terephthalic acid and the isomer mixture of 2,2,4- and 2,4,4-trimethyl hexamethylenediamine.

Instead of using pure 4,4'-diaminodicyclohexyl methane, it is also possible to use mixtures of the position-isomeric diaminodicyclohexyl methanes which consist of 70 to 99 mol-% of the 4,4'-diamino isomer, 1 to 30 mol-% of the 2,4'-diamino isomer, 0 to 2 mol-% of the 2,2'-diamino isomer and, optionally, corresponding more highly condensed diamines obtained by hydrogenation of diaminodiphenyl methane of technical quality.

Suitable thermoplastic polyamides may also consist of mixtures of partially crystalline and amorphous polyamides, the amorphous polyamide component being smaller than the partially crystalline polyamide component. The amorphous polyamides and their production are also known from the prior art (cf. for example Ullmann, Enzyklopädie der technischen Chemie, Vol. 19, page 50).

Preferred other thermoplastics (b) also include thermoplastic, linear or branched polyarylene sulfides. They have structural units corresponding to the following general formula

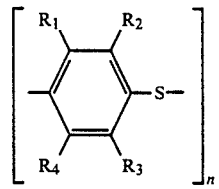

in which $R_1$ and $R_4$ are equal or different and represent $C_1$–$C_6$ alkyl, phenyl or hydrogen. The polyarylene sulfides may also contain diphenyl units.

Polyarylene sulfides and their production are known (see for example US-PS 3,354,129 and EP-A 0 171 021).

Further preferred other thermoplastics (b) are thermoplastic polyarylene sulfones.

Suitable polyarylene sulfones have average weight average molecular weights $\overline{M}w$ (as measured by the scattered light method in $CHCl_3$) of 1,000 to 200,000 preferably 20,000 to 60,000.

Examples are the polyarylene sulfones obtainable in known manner from 4,4'-dichlorodiphenyl sulfone and a bisphenol, particularly 2,2-bis-(4-hydroxyphenyl)-propane, which have average weight average molecular weights $\overline{M}w$ of from 2,000 to 200,000.

These polyarylene sulfones are known (cf. for example US-PS 3,264,536, DE-AS 1 794 171, GB-PS 1,264,900, US-PS 3,641,207, EP-A-0 038 028, DE-OS 3 601 419 and DE-OS 3 601 420). The suitable polyarylene sulfones may also be branched in known manner (cf. for example DE-OS 2 305 413).

Preferred other thermoplastics (b) also include thermoplastic polyphenylene oxides, preferably poly-(2,6-dialkyl-1,4-phenylene oxides). Polyphenylene oxides suitable for the purposes of the invention have weight average molecular weights $\overline{M}w$ (as measured by the scattered light method in chloroform) of from 2,000 to 100,000 and preferably from 20,000 to 60,000. These polyphenylene oxides are known.

The preferred poly-(2,6-dialkyl-1,4-phenylene oxides) may be obtained in known manner by oxidizing condensation of 2,6-dialkylphenols with oxygen in the presence of catalyst combinations of copper salts and tertiary amines (see for example DE-OS 21 26 434 and US-PS 3,306,875).

Suitable poly-2,6-dialkyl-1,4-phenylene oxides) are, in particular, the poly-[2,6-di-($C_1$–$C_4$-alkyl)-1,4-phenylene oxides], such as for example poly-(2,6-dimethyl-1,4-phenylene oxide).

Preferred other thermoplastics (b) also include aromatic polyether ketones (cf. for example GB-PS 1,078,234, US-PS 4,010,147 and EP-OS 0 135 938).

They contain the recurring structural element

—O—E—O—E'— in which —E'— is the residue of a bisaryl ketone having two bonds and —O—E—O— is a diphenolate residue having two bonds.

They may be obtained, for example, in accordance with GB-PS 1,078,234 from dialkali diphenolates having the formula alkali —O—E—O—alkali and bis-(haloaryl)-ketones having the formula hal-E'-hal (hal=-halogen). One suitable dialkali diphenolate is, for example, that of 2,2-bis-(4-hydroxyphenyl)-propane, while a suitable bis-(haloaryl)-ketone is 4,4'-dichlorobenzophenone.

Preferred other thermoplastics (b) also include thermoplastic vinyl polymers.

Vinyl polymers in the context of the invention are homopolymers of vinyl compounds, copolymers of vinyl compounds and graft polymers of vinyl compounds on rubbers.

Homopolymers and copolymers suitable for the purposes of the invention and those of styrene, α-methyl styrene, acrylonitrile, methacrylonitrile, $C_1$–$C_{12}$ (cyclo)alkyl esters of (meth)acrylic acid, $C_1$–$C_4$-carboxylic acid vinyl esters, the copolymers also being obtainable from mixtures of these vinyl compounds by known methods.

The homopolymers or copolymers should have intrinsic viscosities of from 0.3 to 1.5 dl/g (as measured at 23° C. in toluene in known manner).

Suitable vinyl polymers are, for example, thermoplastic poly-$C_1$–$C_4$-alkyl methacrylates, for example those of methyl, ethyl, propyl or butyl methacrylate, preferably methyl or ethyl methacrylate. Both homopolymers and copolymers of these methacrylates are included. In addition, other ethylenically unsaturated, copolymerizable monomers, such as for example (meth)acrylonitrile, (α-methyl) styrene, bromostyrene, vinyl acetate, $C_1$–$C_8$ alkyl acrylate, (meth)acrylic acid, ethylene, propylene and N-vinyl pyrrolidone, may be copolymerized in small quantities.

The thermoplastic poly-$C_1$–$C_4$-alkyl methacrylates suitable for the purposes of the invention are known from the literature or may be obtained by methods known from the literature.

Suitable vinyl polymers also include copolymers of styrene or α-methyl styrene and acrylonitrile optionally containing up to 40% by weight of esters of acrylic or methacrylic acid, particularly methyl methacrylate or n-butyl acrylate. Styrene derivatives must always be present as monomers. The styrene derivatives are present in proportions of 100 to 10% by weight, preferably 90 to 20% by weight and more preferably 80 to 30% by weight and may be obtained by standard methods, such as radical polymerization in bulk, solution, suspension or emulsion, but preferably by radical emulsion polymerization in water.

Suitable graft polymers are formed by polymerization of the above-mentioned vinyl monomers or mixtures of vinyl monomers in the presence of rubbers having glass temperatures below 0° C. and preferably below −20° C. The graft polymers generally contain 1 to 85% by weight and preferably 10 to 80% by weight rubber. The graft polymers may be prepared by standard methods in solution, bulk or emulsion, preferably in emulsion; mixtures of vinyl monomers may be simultaneously or successively graft-polymerized.

Suitable rubbers are, preferably, diene rubbers and acrylate rubbers.

Diene rubbers are, for example, polybutadiene, polyisoprene and copolymers of butadiene with up to 35% by weight comonomers, such as styrene, acrylonitrile, methyl methacrylate and $C_1$–$C_6$ alkyl acrylates.

Acrylate rubbers are, for example, crosslinked, particulate emulsion polymers of $C_1$–$C_6$-alkyl acrylates, particularly $C_2$–$C_6$-alkyl acrylates, optionally in admixture with up to 15% by weight of other unsaturated monomers, such as styrene, methyl methacrylate, butadiene, vinyl methyl ether, acrylonitrile, and of at least one polyfunctional crosslinking agent, such as for example divinylbenzene, glycol-bis-acrylates, bis-acrylamides, phosphoric acid triallyl ester, citric acid triallyl ester, allyl esters of acrylic acid and methacrylic acid, triallyl isocyanurate, the acrylate rubbers containing up to 4% by weight of the crosslinking comonomers.

Mixtures of diene rubbers with acrylate rubbers and also rubbers having a core-shell structure are also suitable for the production of the graft polymers.

For graft polymerization, the rubbers must be present in the form of discrete particles, for example in the form of a latex. These particles generally have mean diameters of from 10 nm to 2000 nm.

The graft polymers may be produced by known methods, for example by radical emulsion graft polymerization of the vinyl monomers in the presence of rubber latices at temperatures of from 50° to 90° C. using water-soluble initiators, such as peroxodisulfate, or redox initiators.

Emulsion graft polymers produced by radical graft polymerization onto particulate, highly crosslinked rubbers (diene or alkyl acrylate rubbers) having gel contents of more than 80% by weight and mean particle diameters ($d_{50}$) of from 80 to 800 nm are preferred.

Technical ABS polymers are particularly suitable.

Mixtures of vinyl homopolymers and/or vinyl copolymers with graft polymers are also suitable.

Preferred other thermoplastics (b) also include thermoplastic polyurethanes. These are reaction products of diisocyanates, completely or predominantly aliphatic oligo- and/or polyesters and/or ethers and one or more chain-extending agents. These thermoplastic polyurethanes are substantially linear and have thermoplastic processing characteristics.

The thermoplastic polyurethanes are known or may be obtained by known methods (cf. for example US-PS 3,214,411; J. H. Saunders and K. C. Frisch, "Polyurethanes, Chemistry and Technology", Vol. II, pages 299 to 451, Interscience Publishers, New York, 1964; and Mobay Chemical Corporation "A Processing Handbook for Texin Urethane Elastoplastic Materials", Pittsburgh, Pa.).

Starting materials for the production of the oligoesters and polyesters are, for example, adipic acid, succinic acid, sebacic acid, suberic acid, oxalic acid, methyl adipic acid, glutaric acid, pimelic acid, azealic acid, phthalic acid, terephthalic acid and isophthali acid.

Adipic acid is preferred.

Suitable glycols for the production of the oligoesters and polyesters are, for example, ethylene glycol, 1,2- and 1,3-propylene glycol, butane-1,2-, -1,3-, -1,4-, -2,3- and -2,4-diol, hexanediol, bis-hydroxymethyl cyclohexane, diethylene glycol and 2,2-dimethyl propylene glycol. In addition, small quantities, i.e. up to 1 mol-%, of trihydric or higher alcohols, for example trimethylol propane, glycerol, hexanetriol etc., may be used together with the glycols.

The resulting hydroxyl oligoesters or polyesters have a molecular weight of at least 600, a hydroxyl value of from about 25 to 190 and preferably from about 40 to 150, an acid value of from about 0.5 to 2 and a water content of from about 0.01 to 0.2%.

Oligoesters and polyesters also include oligomeric or polymeric lactones, such as for example oligocaprolactone or polycaprolactone, and aliphatic polycarbonates, such as for example polybutane-1,4-diol carbonate or polyhexane-1,6-diol carbonate.

A particulaly suitable oligoester which may be used as starting material for the thermoplastic polyurthanes is prepared from adipic acid and a glycol containing at least one primary hydroxyl group. The condensation is terminated when an acid value of 10 and preferably of about 0.5 to 2 is reached. The water formed during the reaction is thus separated off simultaneously or afterwards, so that the final water content is between about 0.01 to 0.05% and preferably between 0.01 to 0.02.

Oligoethers and polyethers for the production of the thermoplastic polyurethanes are, for example, those based on tetramethylene glycol, propylene glycol and ethylene glycol.

Polyacetals may also be regarded as polyethers and may be used as such.

The oligoethers or polyethers should have average molecular weights $\overline{Mw}$ (number average determined via the OH value of the products) of from 600 to 2,000 and preferably from 1,000 to 2,000.

4,4′-Diphenyl methane diisocyanate is preferably used as the organic diisocyanate for the production of the polyurethanes. It should contain less than 5% 2,4′-diphenyl methane diisocyanate and less than 2% of the dimer of diphenyl methane diisocyanate. In addition, the acidity, expressed as HCl, should be in the range from about 0.005 to 0.2%. The acidity expressed as % HCl is determined by extraction of the chloride from the isocyanate in hot, aqueous methanol solution or by liberation of the chloride during hydrolysis with water and titration of the extract with standard silver nitrate solution in order to obtain the concentration of chloride ions present therein.

It is also possible to use other diisocyanates for the production of the thermoplastic polyurethanes, including for example the diisocyanates of ethylene, ethylidene, propylene, butylene, cyclo-1,3-pentylene, cyclo-1,4-hexylene, cyclo-1,2-hexylene, 2,4-tolylene, 2,6-tolylene, p-phenylene, n-phenylene, xylene, 1,4-naphthylene, 1,5-naphthylene, 4,4′-diphenylene; 2,2-diphenylpropane-4,4′-diisocyanate, azobenzene-4,4′-diisocyanate, diphenylsulfone-4,4′-diisocyanate, dichlorohexamethylene diisocyanate, pentamethylene diisocyanate, hexamethylene diisocyanate, 1-chlorobenzene-2,4-diisocyanate, furfuryl diisocyanate, dicyclohexyl methane diisocyanate, isophorone diisocyanate, diphenyl ethane diisocyanate and bis-(isocyanatophenyl)-ethers of ethylene glycol, butanediol, etc.

Suitable chain-extending agents are organic difunctional compounds containing active hydrogen reactive to isocyanates, for example diols, hydroxycarboxylic acids, dicarboxylic acids, diamines and alkanolamines and water. Examples of such chain-extending agents are, for example, ethylene, propylene and butylene glycol, butene-1,4-diol, butanediol, butynediol, xylylene glycol, amylene glycol, 1,4-phenylene-bis-β-hydroxyethyl ether, 1,3-phenylene-bis-β-hydroxyethyl ether, bis-(hydroxymethylcyclohexane), hexanediol, adipic acid, Ω-hydroxycaproic acid, thiodiglycol, ethylenediamine, propylene, butylene, hexamethylene, cyclohexylene, phenylene, tolylene and xylylenediamine, diaminodicyclohexyl methane, isophoronediamine, 3,3′-dichlorobenzidine, 3,3′-dinitrobenzidine, ethanolamine, aminopropyl alcohol, 2,2-dimethyl propanolamine, 3-aminocyclohexyl alcohol and p-aminobenzyl alcohol. The molar ratio of oligoester or polyester to bifunctional chain extender is in the range from 1:1 to 1:50 and preferably in the range from 1:2 to 1:30.

In addition to difunctional chain-extending agents, it is also possible to use trifunctional or more than trifunctional chain-extending agents in small quantities of up to about 5 mol-%, based on mols of difunctional chain-extending agents used.

Examples of trifunctional or ore then trifunctional chain-extending agents are glycerol, trimethylol propane, hexanetriol, pentaerythritol and triethanolamine.

Monofunctional components, for example butanol, may also be used for the production of the thermoplastic polyurethanes.

The diisocyantes, oligoesters, polyesters, polyethers, chain-extending agents and monofunctional components mentioned as structural units for the thermoplastic polyurethanes are either known from the literature or may be obtained by methods known from the literature.

The known production of the polyurethanes may be carried out, for example, as follows:

For example, the oligoesters or polyesters, the organic diisocyanates and the chain-extending agents may be individually heated, preferably to a temperature of from about 50° to 220° C., and then mixed. The oligoesters or polyesters are preferably first individually heated, then mixed with the chain-extending agents and the resulting mixture mixed with the preheated isocyanate.

The starting components for the production of the polyurethane may be mixed by any mechanical stirrer which provides for intensive mixing in a short time. If the viscosity of the mixture should prematurely rise too quickly during stirring, either the temperature may be lowered or a small quantity (0.001 to 0.05% by weight, based on ester) citric acid or the like may be added to reduce the reaction velocity. To increase the reaction velocity, suitable catalysts, such as for example the tertiary amines mentioned in US-PS 2,729,618, may be used.

Preferred other thermoplastics are also so-called "LC" polymers. LC polymers are polymers capable of forming liquid liquid crystalline melts. Polymers of this type, which are also termed "thermotropic", are sufficiently well-known (see for example EP-OS 0 131 846, EP-OS 0 132 637 and EP-OS 0 134 959). More literature is cited in these literature references which also describe determination of the liquid crystalline state of polymer melts.

Examples of the LC polymers are aromatic polyesters based on optionally substituted p-hydroxybenzoic acid, optionally substituted iso- and/or terephthalic acids, 2,7-dihydroxynaphthalene and other diphenols (EP-OS 0 131 846), aromatic polyesters based on optionally substituted p-hydroxybenzoic acid, diphenols, carbonic acid and, optionally, aromatic dicarboxylic acids (EP-OS 0 132 637) and aromatic polyesters cased on optionally substituted p-hydroxybenzoic acid, 3-chloro-4-hydroxybenzoic acid, isophthalic acid, hydroquinone and 3,4'- and/or 4,4'-dihydroxydiphenyl, 3,4'- and/or 4,4'-dihydroxydiphenyl ether and/or 3,4'-and/or 4,4'-dihydroxydiphenyl sulfide (EP-OS 0 134 959).

The LC polymers have a persistence length at room temperature of from 18 to 1300 Å, preferably from 25 to 300 Å and more preferably from 25 to 150 Å.

The persistence length of a polymer at room temperature characterizes the average entanglement of a molecular chain in a dilute solution under theta conditions (cf. for example P. J. Flory, Principles of Polymer Chemistry, Cornell Univ. Press. Ithaca, N.Y.) and half Kuhn's step length. The persistence length may be determined by various methods in dilute solutions, for example by light scattering and X-ray small angle measurements. After suitable preparation, the persistence length may also be determined by neutron small angle scattering in the solid. Other theoretical and experimental methods are described, for example, in J. H. Wendorff in "Liquid Crystalline Order in Polymers", e.g. A. Blumstein, Academic Press 1978, pages 16 et seq, and in the references cited in S. M. Aharoni, Macromolecules 19, (1986), pages 429 et seq.

Preferred other theromplastics include aromatic polyester carbonate.

Aromatic polyesters and polyester carbonates which can be used according to the invention as thermoplastic (b) are composed of at least one aromatic bisphenol, for example of the formula (VII), of at least one aromatic dicarboxylic acid and optionally of carbonic acid. Suitable aromatic dicarboxylic acids are, for example, orthophthalic acid, terephthalic acid, isophthalic acid, tert.-butylisophthalic acid, 3,3'-diphenyldicarboxylic acid, 4,4'-diphenyldicarboxylic acid, 4,4'-benzophenonedicarboxylic acid, 3,4'-benzophenonedicarboxylic acid, 4,4'-diphenyl ether dicarboxylic acid, 4,4'-diphenylsulphone dicarboxylic acid, 2,2-bis-(4-carboxyphenyl)-propane and trimethyl-3-phenylindane-4,5'-dicarboxylic acid.

Of the aromatic dicarboxylic acids terephthalic acid and/or isophthalic acid are particularly preferably used.

Aromatic polyesters and polyester carbonates can be prepared by processes which are kown from the literature for the production of polyesters and polycarbonates, such as for example by process in homogeneous solution, by transesterification processes in the melt and by the two-phase interface process. Transesterification processes in the melt and in particular the two-phase interface process are preferably employed.

Transesterification processes in the melt (the acetate process and the phenyl ester process) are described for example in U.S. Pat. Nos. 3,494,885, 4,386,186, 4,661,580, 4,680,371 and 4,680,372, European Patent Applications Nos. 26,120, 26,121, 26,684, 28,030, 39,845, 91,602, 97,970, 79,075, 146,887, 156,103, 234,913, 234,919 and 240,301 and German Published Specifications Nos. 1,495,626 and 2,232,877. The two-phase interface process is described for example in European Applications Nos. 68,014, 88,322, 134,898, 151,750, 182,189, 219,708, 272,426, in German Offenlegungsschrifts No. 2,940,024, 3,007,934, 3,440,020 and in Polymer Reviews, Volume 10, "Condensation Polymers by Interfacial and Solution Methods", Paul W. Morgan, Interscience Publishers, New York 1965, Chapter (VIII), page 325, Polyesters.

In the acetate process it is generally bisphenol diacetate and in the phenyl ester process it is generally bisphenol, aromatic diarboxylic acid or diphenyl esters of aromatic dicarboxylic acid and optionally diphenyl carbonate which are reacted, with the elimination of phenol and where appropriate with the elimination of $CO_2$, to form the polyester or polyester carbonate. In the two-phase interface process the starting materials generally used for the production of polyesters and polyester carbonates are alkali metal bisphenolate, aromatic dicarboxylic acid dichloride and optionally phosgene. In this condensation reaction the polyester of the polyester carbonate are produced with the formation of alkali metal chloride. In general the salt formed is dissolved in the aqueous phase, whereas the polyester formed or the polyester carbonate formed are present in a solution in the organic phase and are isolated therefrom.

Preferred elastomers (b3) for component (b) for the production of the mixtures according to the invention are the polyurethanes mentioned above, providing they are elastic, styrene-butadiene block copolymers which may be partially hydrogenated (for example Kraton G ®, a Shell product), the rubbers mentioned above for the graft polymers, the graft polymers themselves, providing they are elastic, and elastic polycarbonate-polyether block copolymers.

These elastomers are known.

The films or composite films may be flat, hollow, spherical, tubular and hollow-fiber-like. Films such as these are obtainable in known manner by thermoforming, deep drawing, blowing etc.

The films according to the invention, particularly the composite films, are used for example for boil-proof and oven-proof, leak-proof packs and for microwave-oven-proof packs, depending on which component (b) is used for the composite film according to the invention.

The composite films according to the invention may be produced by co-extrusion of the thermoplastics with the polycarbonates of the invention in a single operation.

The films according to the invention of polycarbonates of the invention and the composition films according to the invention based on these films of the polycarbonates (a) may be used as homogeneous membranes, composition membranes or asymmetrical membranes.

In the working examples the relative viscosity was measured on 0.5% by weight solutions of the polycarbonate in $CH_2Cl_2$.

The glass temperature was measured by differential scanning calorimetry (DSC).

EXAMPLE B.1

31.0 g (0.1 mol) of the diphenol of Example A.1, 33.6 g (0.6 mol) KOH and 560 g water are dissolved while stirring in an inert gas atmosphere. A solution of 0.188 g phenol in 560 ml methylene chloride is then added. 19.8 g (0.2 mol) phosgene were introduced into the thoroughly stirred solution at pH 13 to 14 and at 21° to 25° C. 0.1 ml ethyl pyridine is then added, followed by stirring for 45 minutes. The bisphenolate-free aqueous phase is separated off, the organic phase is washed with water until neutral after acidification with phosphoric acid and is freed from solvent. The polycarbonate had a relative solution viscosity of 1.259.

The glass temperature of the polymer was found to be 233° C. (DSC).

EXAMPLE B.2

68.4 g (0.3 mol) bisphenol A (2,2-bis-(4-hydroxyphenyl)-propane, 217.0 g (0.7 mol) diphenol of Example A.3, 336.6 g (6 mol) KOH and 2700 g water are dissolved with stirring in an inert gas atmosphere. A solution of 1.88 g phenol in 2500 ml methylene chloride is then added. 198 g (2 mol) phosgene were introduced into the thoroughly stirred solution at pH 13 to 14 and at 21° to 25° C. 1 ml ethyl piperidine is then added, followed by stirring for 45 minutes. The bisphenolate-free aqueous phase is separated off, the organic phase is washed with water until neutral after acidification with phosphoric acid and is freed from the solvent. The polycarbonate had a relative viscosity of 1.336.

The glass temperature of the polymer was found to be 212° C. (DSC).

EXAMPLE B.3

A mixture of 114 g (0.5 mol) bisphenol A and 155 g (0.5 mol) of the diphenol of Example A.1 was reacted as in Example B.2 to form the polycarbonate.

The polycarbonate had a relative solution viscosity of 1.386.

The glass temperature of the polymer was found to be 195° C. (DSC).

EXAMPLE B.4

A mixture of 159.6 g (0.7 mol) bisphenol A and 93 g (0.3 mol) of the diphenol of Example A.3 was reacted as in Example B.2 to form the polycarbonate.

The polycarbonate had a relative solution viscosity of 1.437.

The glass temperature of the polymer was found to be 180° C. (DSC).

EXAMPLE B.5

31.0 g (0.1 mol) of the diphenol of Example A.3, 24.0 g (0.6 mol) NaOH and 270 g water are dissolved with stirring in an inert gas atmosphere. A solution of 0.309 g 4-1,1,3,3-tetramethylbutyl)-phenol in 250 ml methylene chloride is then added. 19.8 g (0.2 mol) phosgene were introduced into the thoroughly stirred solution at pH 13 to 14 and at 21° to 25° C. 0.1 ml ethyl piperidine is then adde, followed by stirring for 45 minutes. The bisphenolate-free aqueous phase is separated off, the organic phase is washed with water until neutral after acidification with phosphoric acid and is free from the solvent. The polycarbonate had a relative solution viscosity of 1.314.

The glass temperature of the polymer was found to be 234° C. (DSC).

To assess the UV stability of the new polycarbonates, the formation of primary radicals under UV irradiation with a mercury vapor lamp (edge filter 305 nm) was determined in comparison with a polycarbonate based on 2,2-bis-(4-hydroxyphenyl)-propane. It was found that the polycarbonate of Example B.1 shows a lower primary radical formation rate and, therefore, higher UV stability.

EXAMPLE B.6

148.2 g (0.65 mol) of 2,2-bis-(4-hydroxyphenyl)-propane, 108.5 g (0.35 mol) of the diphenol of Example A.1, 336,6 g (6 mols) of KOH and 2700 g of water are dissolved with stirring in an inert gas atmosphere. Then a solution of 8.86 g of 4-(1,1,3,3-Tetramethylbutyl)phenol in 2500 of methylene chloride is added. 198 g (2 mols) of phosgene are introduced into the thoroughly stirred solution at a pH of 13-14 and at a temperature of 21°-25° C. Then 1 ml of ethyl piperidine is added and the mixture is stirred for a further 45 minutes. The bisphenolate-free aqueous phase is separated off, the organic phase is washed with water until neutral after acidification with phosphoric acid and is freed from the solvent. The polycarbonate had a relative solution viscosity of 1.20.

EXAMPLE B.7

3.875 kg (12.5 mol) of the bisphenol of Example A.2 are dissolved with stirring under an inert gas atmosphere in 6.375 kg of 45% NaOH and 30 l of water. Then 9.43 l of methylene chloride, 11.3 l of chlorobenzene and 23.5 g of phenol are added. 2.475 kg of phosgene are introduced into the well-stirred solution at a pH of 13-14 and at 20°-25° C. After the introduction is complete 12.5 ml of N-ethylpiperidine are added. The mixture is then left to react for 45 minutes. The bisphenolate-free aqueous phase is separated off, the organic phase is acidified with phosphoric acid and then washed until free from eletrolytes and freed from solvent.

relative viscosity: 1,300
glass transition temperature: 238° C.

EXAMPLE B.8

15.5 g (0.05 mol) of the bisphenol of Example A.3, 13.4 g (0.05 mol) of bis-(4-hydroxyphenyl)-cyclohexane (bisphenol Z) and 24.0 g (0.6 mol) of NaOH are dissolved with stirring in 362 ml of water under an inert gas atmosphere. Then 0.516 g of 4-(1,1,3,3-tetramethylbutyl)phenol dissolved in 271 ml of methylene chloride is added. 19.8 g of phosgene are introduced at a pH of 13-14 and at 20°-25° C. into the well-stirred solution. 5 minutes after the introduction is complete 0.1 ml of N-ethylpiperidine are added. The mixture is then left to react for 45 mins. The bisphenolate-free aqueous phase is separated off and the organic phase is acidified with phosphoric acid and then washed until neutral and freed from solvent.

relative viscosity: 1,297
glass transition temperature: 208° C.

EXAMPLE B.9

15.5 g (0.05 mol) of the bisphenol of Example A.1, 17.6 g (0.05 mol) of 4,4'-dihydroxytetraphenylmethane and 24.0 g (0.6 mol) of NaOH are dissolved with stirring in 411 of water under an inert gas atmosphere. Then 0.516 g of 4-(1,1,3,3-tetramethylbutyl)-phenol dissolved in 308 ml of methylene chloride are added. 19.8 g of phosgene are introduced into the well-stirred solution at a pH of 13-14 and at 20°-25° C. 5 minutes after the introduction is complete 0.1 ml of N-ethylpiperidine is added. The mixture is then left to react for 45 minutes. The bisphenolate-free aqueous phase is separated off and the organic phase is acidified with phosphonic acid and then washed until neutral and freed from solvent.

relative viscosity : 1.218
glass transition temperature: 212° C.

EXAMPLE B.10

18.3 g (0.05 mol) of the bisphenol of Example A.4 and 23.6 (0.42 mol) of KOH are dissolved with stirring in 100 ml of water under an inert gas atmosphere. Then 100 ml of methylene chloride are added. 17.3 g of phosgene ar introduced into the well-stirred solution at a pH of 13-14 and at 20°-25° C. 5 minutes after the introduction is complete 0.3 ml of N-ethylpiperidine is added. The mixture is then left to react for 45 minutes. The bisphenolate-free aqueous phase is separated off and the organic phase is acidified with phosphoric acid and then washed until neutral and freed from solvent.

relative viscosity: 1.310
glass transition temperature: 241° C.

EXAMPLE B.11

29.6 g (0.1 mol) of the bisphenol of Example A.5 and 24.0 (0.6 mol) of NaOH are dissolved with stirring in 370 ml of water under an inert gas atmosphere. Then 0.413 g of 4-(1,1,3,3-tetramethylbutyl)phenol dissolved in 277 ml of methylene chloride are added 19.8 g of phosgene are introduced into the well-stirred solution at a pH of 13-14 and at 20°-25° C. 5 minutes after the introduction is complete 0.1 ml of N-ethylpiperidine are added. The mixture is then left to react for 45 minutes. The bisphenolate-free aqueous phase is separated off and the organic phase is acidified with phosphoric acid and then washed until neutral and freed from solvent.

relative viscosity: 1.370
glass transition temperature: 193° C.

EXAMPLE B.12

62.0 g (0.2 mol) of bisphenol A.1, 182.4 g (0.8 mol) of bisphenol A and 240 g (6 mol) of NaOH are dissolved with stirring in 2400 ml of water under an inert gas atmosphere. Then 6.603 g of 4-(1,1,3,3-tetramethylbutyl)-phenol dissolved in 2400 ml of methylene chloride are added. 198 g of phosgene are introduced into the well-stirred solution at a pH of 13-14 and at 20°-25° C. 5 minutes after the introduction is complete 1 ml of N-ethylpiperidine is added. The mixture is then left to react for 45 minutes. The bisphenolate-free aqueous phase is separated off and the organic phase is acidified with phosphoric acid and then washed until neutral and freed from solvent.

relative viscosity: 1.298
glass transition temperature: 172° C.

EXAMPLE B.13

170.5 g (0.55 mol) of the bisphenol of Example A.3, 102.6 g (0.45 mol) of bisphenol A and 240 g (6 mol) of NaOH are dissolved with stirring in 2400 ml of water under an inert gas atmosphere. Then 5.158 g of 4-(1,1,3,3-tetramethylbutyl)-phenol dissolved in 2400 ml of methylene chloride are added. 198 g of phosgene are introduced into the well-stirred solution at a pH of 13-14 and at 20°-25° C. 5 minutes after the introduction is complete 1 ml of N-ethylpiperidine is added. The mixture is then left to react for 45 minutes. The bisphenolate-free aqueous phase is separated off and the organic phase is acidified with phosphoric acid and then washed until neutral and freed from solvent.

relative viscosity: 1.302
glass transition temperature: 203° C.

EXAMPLE B.14

108.5 g (0.35 mol) of the bisphenol of Example A.1, 148.2 g (0.65 mol) of bisphenol A and 240 g (6 mol) of NaOH are dissolved with stirring in 2400 ml of water under an inert gas atmosphere. Then 6.189 g of 4-(1,1,3,3-tetramethylbutyl)-phenol dissolved in 2400 ml of methylene chloride are added. 198 g of phosgene are introduced into the well-stirred solution at a pH of 13-14 and at 20°-25° C. 5 minutes after the introduction is complete 1 ml of N-ethylpiperidine is added. The mixture is then left to react for 45 minutes. The bisphenolate-free aqueous phase is separated off and the organic phase is acidified with phosphoric acid and then washed until neutral and freed from solvent.

relative viscosity: 1.305
glass transition temperature: 185° C.

EXAMPLE C

Compact discs with a diameter of 12 cm were produced from the copolycarbonate of Example B.6 and from a bisphenol A homopolycarbonate with $\eta_{rel} = 1.20$ in a Netstal injection-moulding machine (bulk temperature 330° to 350° C.). The birefringence of both discs in an axial direction was examined with the aid of a polarising microscrope by means of path difference measurements using a conventional comparator. The transparency was assessed vissually and the glass transition temperature was determined by DSC.

| Material | Path difference [nm/mm] | Tg [°C.] | Transparency |
|---|---|---|---|
| Example B 6 | +13 | 185 | yes |
| Bisphenol-A-polycarbonate | +12 | 145 | yes |

EXAMPLE D.1 (manufacture of a film)

20 g of the polycarbonate of Example B1 were dissolved in 200 ml of methylene chloride with continuous stirring at 30° C., the solution was thickened and a 204 μm thick film was prepared therefrom by casting onto a flat glass plate at 25° C. The film was dried in vacuo for 4 hours at 90° C. The gas permeability of the film was then measured.

Determination of the permeability to gases (permeation) of polymer membranes

The passage of a gas through an impervious polymer membrane is described by a dissolving/diffusion process. The characteristic constant for this process is the permeation P which indicates the gas volume V which passes through a film of known surface area F and thickness d in a certain time t for a given pressure difference Δp. For the steady state, the following may be deduced from the differential equations of the permeation process:

$$P = \frac{V \cdot d}{F \cdot t \cdot \Delta p} \quad (1)$$

In addition, Permeation is dependent on temperature and water content of the gas.

The measuring arrangement consists of a thermostatically controlled 2-chamber system. One chamber is designed to accomodate the test gas and the other to accomodate the permeate. The two chambers are separated by the membrane to be measured.

The two chambers are evacuated to $10^{-3}$ mbar and the first chamber at filled with gas. The permeated gas (inert gas) then produces an increase in pressure in the permeate chamber at constant volume, the increase in pressure being quantitatively recorded by a pressure recorder (an MKS Baratron) as a function of time until the passage of gas reaches the steady state. From the pressure increase V is calculated for normal pressure and temperature. Δp is adjusted to $10^5$ pas taking into account the outside air pressure. The surface area of the membrane F is known. The membrane thickness d is determined by micrometer gauge as the mean value of ten independent thickness measurements distributed over the membrane surface.

From these values, the permeation coefficient P is determined in accordance with (1) with the following dimension:

$$\left[\frac{cm^3 \ (NTP) \cdot mm}{m^2 \cdot 24h \ 10^5 \ Pa}\right]$$

based on the membrane thickness of 1 mm.
Further measurement parameters are:
Temperature: $25° \pm 1°$ C.
Relative gas humidity: 0%
Result: permeation coefficient
  for $O_2$: 280,8
  for $N_2$: 84,5
  for $CO_2$: 2174,0
  for $CH_4$: 149,4
The film was still dimensionally stable at 180° C.

EXAMPLE D.2 (Comparison Example)

A film was prepared as in Example 3 from bisphenol-A-polycarbonate having a relative viscosity of 1.28 (thickness 154 μm) and measured.
Result: permeation coefficient
  for $O_2$: 72,0
  for $N_2$: 366,0
  for $CO_2$: 35,0
  for $CH_4$: 27,0
This film was not dimensionally stable at 180° C.

EXAMPLE D.3

As described in Example D.1 a film with a thickness of 92 μm is produced from 20 g of the polycarbonate of Example B.12 and its gas permeability is then measured.

EXAMPLE D.4

As described in Example D.1 a film with a thickness of 95 μm is produced from 20 g of the polycarbonate of Example B.13 and its gas permeability is then measured.

EXAMPLE D.5

As described in Example D.1 a film with a thickness of 89.7 μm is produced from 20 g of the polycarbonate of Example B.14 and its gas permeability is then measured.

EXAMPLE D.6

The polycarbonate of Example B.7 is melted in an extruder (temperature: 360°-370° C.) and is extruded through a flat sheet die to form a film with a thickness of 163 μm, the gas permeability of which is then measured.

EXAMPLE D.7

31 g (0.1 mol) of bisphenol of Example A.1 and 24 g (0.6 mol) of NaOH are dissolved with stirring in 270 ml of water under an inert gas atmosphere. Then 250 ml of methylene chloride are added. 19.8 g of phosgene are introduced into the well-stirred solution at a pH of 13-14 and at 20°-25° C. 5 minutes after the introduction is complete 0.1 ml of N-ethylpiperidine is added. The mixture is then left to react for 45 minutes. The bisphenolate-free aqueous phase is separated off and the organic phase is acidified with phosphoric acid and then washed until neutral. From the concentrated solution in methylene chloride a film was cast which displayed clear transparency. GPC-analysis: The molecular weight was determined on the basis of calibration with bisphenol-A polycarbonate.
$M_w = 246,000$, $M_n = 38,760$
Permeation coefficient:

| Sample | Permeation gases | | | |
|---|---|---|---|---|
| | $N_2$ | $O_2$ | $CO_2$ | $CH_4$ |
| D.3 | 23.9 | 109.2 | 634.9 | 30.2 |
| D.4 | 49.7 | 227.9 | 1629.5 | 64.3 |
| D.5 | 33.6 | 138.8 | 828.1 | 46.8 |
| D.6 | 78.2 | 400.5 | 2555.0 | n.d. | n.d.: not determined.

EXAMPLE D8 (composite film)

After evaporation of the solvent, films prepared at 235° C. in accordance with Examples D1 and D2 were superposed and pressed together for 4 minutes under a pressure of about 234 bar and at a temperature of 235° C. to form a film approximately 307 μm thick. Gas permeability was measured as described in Example D1.
Result: permeation coefficient
  for $O_2$: 208,3
  for $CO_2$: 1209,4
  for $CH_4$: 77,1
This composite film was also still dimensionally stable at 180° C.

EXAMPLE D.9

Composite film of polycarbonate of Example B.14 and polymethyl methacrylate.

A polymethyl methacrylate film (PMMA) with a thickness of 130 μm and a film of polycarbonate of Example B.14 with a thickness of 131 μm are preheated for 30 seconds and are then pressed together at 160° C. for 30 seconds under a bonding pressure of 200 bars to form a composite film with a thickness of 200 μm. The gas permeability of the composite film was measured as described in Example D.1.

EXAMPLE D.10

Composite film of polycarbonate of Example B.14 and polystyrene

A polystyrene film (polystyrene N 168 manufactured by BASF AG) with a thickness of 78 μm and a film produced from the polycarbonate of Example B.14 with a thickness of 101 μm are preheated for 30 seconds and are then pressed together at 160° C. for 30 seconds under a bonding pressure of 200 bar to form a composite film of a thickness of 168 μm. The gas permeability of the composite film was measured as described in Example D.1.

Permeation coefficients:

| Sample | Permeation gases | | | |
|---|---|---|---|---|
| | $N_2$ | $O_2$ | $CO_2$ | $CH_4$ |
| D.9 | 0.7* | 4.5 | 20.3 | 0.42* |

-continued

| Sample | Permeation gases | | | |
|---|---|---|---|---|
| | $N_2$ | $O_2$ | $CO_2$ | $CH_4$ |
| D.10 | 18.0 | 102.9 | 488.5 | 25.6 |

\* = As in the case of this composite film a very slight increase in pressure was observed after the introduction of the gas into the measuring cell the value of permeation from the permeate was determined after a permeation time of 3 days.

We claim:

1. Dihydroxydiphenyl cycloalkanes corresponding to the formula

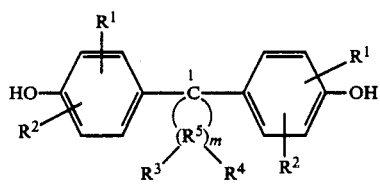

(I)

in which $R^1$ and $R^2$ independently of one another represent hydrogen, halogen, $C_1$–$C_8$-alkyl, $C_5$–$C_6$ cycloalkyl, $C_5$–$C_{10}$-aryl and $C_7$–$C_{12}$ aralkyl, m is an integer of from 4 to 7, $R^3$ and $R^4$, individually selectable for each X, independently of one another represent hydrogen of $C_1$–$C_6$-alkyl and $R^5$ represents carbon, with the proviso that, at at least one atom $R^5$, both $R^3$ and $R^4$ are alkyl.

2. Dihydroxydiphenyl cycloalkanes corresponding to formula (I) as claimed in claim 1, wherein neither of the two $R^5$ atoms in the α-position to C-1 is dialkyl-substituted.

3. Dihydroxydiphenyl cycloalkanes corresponding to formula (I) as claimed in claim 1, wherein a dialkyl-substituted $R^5$-atom is in the β-position to C-1.

4. Dihydroxydiphenyl cycloalkanes corresponding to formula (I) as claimed in claim 1, wherein m is 4 or 5.

5. 1,1-Bis-(4-hydroxyphenyl)-3,3,5-trimethyl cyclohexane.

* * * * *